(12) United States Patent
Schuschnig et al.

(10) Patent No.: US 8,347,878 B2
(45) Date of Patent: *Jan. 8, 2013

(54) AEROSOL THERAPY DEVICE

(75) Inventors: Uwe Schuschnig, Munich (DE); Martin Luber, Munich (DE); Wolfgang Achtzehner, Alling (DE)

(73) Assignee: PARI GmbH Spezialisten für effektive Inhalation, Starnberg (DE)

( * ) Notice: Subject to any disclaimer, the term of this patent is extended or adjusted under 35 U.S.C. 154(b) by 1311 days.

This patent is subject to a terminal disclaimer.

(21) Appl. No.: 12/080,843

(22) Filed: Apr. 7, 2008

(65) Prior Publication Data

US 2008/0251068 A1    Oct. 16, 2008

(30) Foreign Application Priority Data

Apr. 11, 2007   (EP) ..................................... 07007418

(51) Int. Cl.
*A61M 11/00* (2006.01)
(52) U.S. Cl. ......... 128/200.14; 128/204.23; 128/200.11; 128/203.12; 128/203.15
(58) Field of Classification Search ............. 128/204.23, 128/200.14, 200.11–13, 200.16, 200.18, 128/200.23–24, 203.12, 203.15–19, 203.21–22, 128/204.12, 206.29, 207.13, 207.18; 239/330, 239/310, 322, 338, 350, 337, 586; 222/386, 222/387, 321.1, 321.6–321.8, 381, 391, 327, 222/326, 160, 162, 163; 604/151, 207, 211, 604/131, 209, 232, 208; 606/199, 204.45
See application file for complete search history.

(56) References Cited

U.S. PATENT DOCUMENTS

| | | | |
|---|---|---|---|
| 2,078,180 | A | 4/1937 | Kronenberg |
| 2,582,529 | A | 1/1952 | Curry et al. |
| 4,029,095 | A | 6/1977 | Pena |
| 4,268,460 | A | 5/1981 | Boiarski et al. |
| 4,273,124 | A | 6/1981 | Zimmerman |
| 4,429,835 | A | 2/1984 | Brugger et al. |
| 4,951,661 | A | 8/1990 | Sladek |

(Continued)

FOREIGN PATENT DOCUMENTS

DE    32 38 149 A1    4/1984

(Continued)

OTHER PUBLICATIONS

Extended Search Report issued on Jun. 3, 2008 from European Application No. 1 806 157.

(Continued)

*Primary Examiner* — Justine Yu
*Assistant Examiner* — Colin W Stuart
(74) *Attorney, Agent, or Firm* — Wolf, Greenfield & Sacks, P.C.

(57) ABSTRACT

Aerosol therapy device comprising a nebuliser (10) for generating an aerosol and forming an aerosol flow, a first nosepiece (11) for introducing the aerosol flow into one of the two nostrils (12) of a user, a pressure fluctuation source for generating a pressure fluctuation (DS), a second nosepiece (14) for introducing the pressure fluctuation into the other of the two nostrils (15) of the user in order to superimpose the pressure fluctuation and the aerosol flow, and a sensor system comprising a first pressure sensor (19) for detecting the signal of the pressure fluctuation that arrives at the first nosepiece (11), and an evaluation means (18) that concludes the degree of closure of the velum of the user based on the signal.

7 Claims, 1 Drawing Sheet

U.S. PATENT DOCUMENTS

| | | | |
|---|---|---|---|
| 5,054,477 A | 10/1991 | Terada et al. | |
| 5,584,285 A | 12/1996 | Salter et al. | |
| 5,687,715 A | 11/1997 | Landis et al. | |
| 5,871,009 A | 2/1999 | Rydgren | |
| 5,890,491 A | 4/1999 | Rimkus | |
| 5,928,190 A | 7/1999 | Davis | |
| 6,192,876 B1* | 2/2001 | Denyer et al. | 128/205.25 |
| 6,636,767 B1 | 10/2003 | Knudson | |
| 6,715,485 B1 | 4/2004 | Djupesland | |
| 7,059,320 B2 | 6/2006 | Feiner et al. | |
| 7,225,807 B2 | 6/2007 | Papania et al. | |
| 8,006,698 B2* | 8/2011 | Boehm et al. | 128/207.18 |
| 2005/0193827 A1* | 9/2005 | Fischer et al. | 73/754 |
| 2005/0235992 A1* | 10/2005 | Djupesland | 128/204.18 |
| 2006/0162722 A1 | 7/2006 | Boehm et al. | |
| 2006/0219241 A1* | 10/2006 | Djupesland | 128/200.18 |
| 2007/0095347 A1* | 5/2007 | Lampotang et al. | 128/204.23 |
| 2007/0181133 A1 | 8/2007 | Boehm et al. | |

FOREIGN PATENT DOCUMENTS

| | | |
|---|---|---|
| DE | 36 17 400 A1 | 11/1987 |
| DE | 200 19 479 U1 | 3/2001 |
| EP | 0 507 707 B1 | 10/1992 |
| EP | 0 652 021 A1 | 5/1995 |
| EP | 0 732 111 A2 | 9/1996 |
| EP | 1 180 378 A2 | 2/2002 |
| FR | 1 567 403 | 5/1969 |
| FR | 2 639 236 A1 | 5/1990 |
| WO | WO 00/51672 A1 | 9/2000 |
| WO | WO 01/02024 A1 | 1/2001 |
| WO | WO 01/34232 A1 | 5/2001 |
| WO | WO 03/082393 A1 | 10/2003 |
| WO | WO 2004/004814 A2 | 1/2004 |
| WO | WO 2004020029 A1 * | 3/2004 |

OTHER PUBLICATIONS

H. Kauf, "Ability of Aerosols to Penetrate Paranasal Sinuses", Archiv klin. exper. Ohren-, Nasen- und Kehlkopfheilk., 190, pp. 95-108, 1968.

Hyo et al., Particle deposition efficiency of therapeutic aerosols in the human maxillary sinus, Rhinology, 27, pp. 17-26, 1989.

Search report mailed Dec. 12, 2003 from International Application No. PCT/EP03/09862.

Search report mailed Jul. 6, 2007 from corresponding European Application No. 07007418.2.

* cited by examiner

AEROSOL THERAPY DEVICE

The invention relates to an aerosol therapy device, in which an aerosol generated in a nebuliser is supplied via a nosepiece to the nasal cavities of a patient in the form of an aerosol flow.

It is known in this regard from "*Eindringvermögen von Aerosolen in Nebenräume*" [Ability of Aerosols to Penetrate Paranasal Sinuses], H. Kauff, Archiv klin. exper. Ohren-, Nasen-und Kehlkopfheilk. 190, 95-108 (1968), that pressure fluctuations and vibrations can cause aerosol to penetrate the paranasal sinuses, through which the aerosol flow through the nasal cavities does not otherwise actively flow. An example of the application of these findings is known from EP 0 507 707 A1. According thereto, an aerosol flow is super-imposed with pressure fluctuations, which are supposed to cause aerosol particles/droplets of the aerosol flow to pass through the ostia and enter the paranasal sinuses. In this way, even though the aerosol flow does not directly flow through the paranasal sinuses, they can still be reached and treated by a drug administered in aerosol form. As with other aerosol therapies, it is attempted to deposit sufficient quantities of the drug at the desired sites, for which, in the case of the paranasal sinuses, a sufficient quantity of the aerosol of the aerosol flow must pass through the ostia and penetrate the paranasal sinuses.

Experimental studies on different models of the human nose have shown that when known aerosol therapy devices are used, deposition in the paranasal sinuses is lower than expected and desired. The opening size of the ostia, which is often very small as a result of the illness, also has a strong influence on deposition.

Known from DE 102 39 321 B3 is an aerosol therapy device of the type described above, comprising a nebuliser that has an aerosol generator to which compressed air is supplied for generation of an aerosol flow and a connector for supplying pressure fluctuations that are superimposed on the aerosol flow, and comprising a nosepiece for supplying the aerosol to one of the two alae of the nose/nostrils of a user, which is connected to the nebuliser. A flow resistance device is furthermore provided, with which the flow resistance at the other of the two nostrils of the user is precisely defined. It is only owing to the flow resistance at the other nostril that the superimposed pressure fluctuations cause aerosol from the aerosol flow to also reach the paranasal cavities and be deposited there.

However, the supply of the compressed gas flow and pressure fluctuations as described in DE 102 39 321 B3 requires a specific design of the nebuliser, and thus not every nebuliser is suitable for this use.

In order to eliminate this problem, the subsequently published DE 10 2006 001 113 B describes an aerosol therapy device comprising a nebuliser for generating an aerosol and forming an aerosol flow, a first nosepiece for introducing the aerosol flow to one of the two nostrils of a user, a pressure fluctuation source for generating a pressure fluctuation and a second nosepiece for introducing the pressure fluctuation to the other of the two nostrils of the user in order to superimpose the pressure fluctuation and the aerosol flow.

In particular in an antifungal or antibiotic therapy of the paranasal sinuses, one of the regulatory requirements placed on an aerosol therapy device is the restriction or prevention of erroneous depositions of the active agent in the pharyngeal cavity and the lungs.

In order to meet this requirement, the aerosol therapy device must ensure that aerosol application in the nose only occurs if the velum of the user is closed.

The problem underlying the present invention is based on the provision of an aerosol therapy device in which it is possible to conclude in the simplest manner the degree of closure of the velum of the user.

The idea forming the basis for the present invention is that the pressure fluctuation introduced into one nostril is transmitted, when the velum is closed, through the entire nasal cavity and propagates with little attenuation up to the nebuliser that is located at the other nostril. If the velum is open or only partly closed, the signal of the pressure fluctuation will be highly attenuated on arrival or will be eliminated completely owing to the increase in volume (pharyngeal cavity, lungs, etc) and the additionally increased soft tissue attenuation. That is to say, it can be determined at that nostril into which the aerosol is introduced on the basis of the strength (amplitude) of the arriving pressure fluctuation signal whether the velum is closed to an appropriate degree or not. However, this requires a tight fit between the two nosepieces and the nose, which can also be indirectly evaluated by the present invention (evaluation device).

The above object is solved by an aerosol therapy device of the present invention as is defined in patent claim 1. Advantageous embodiments are specified in the sub-claims.

It is noted that the first and second nosepiece can be formed integrally or separately.

The nebuliser for generating the aerosol preferably comprises a membrane and an electromechanical transducer, in particular a piezoelectric element, having a functional connection to the membrane, with the first pressure sensor that detects the pressure fluctuations arriving at the first nosepiece being formed by these elements. The number of parts can thereby be greatly reduced and the design of the entire aerosol therapy device can thus be simplified. This leads to advantages as regards both assembly and costs. In this embodiment, the introduced pressure fluctuation impinges on the membrane via the first nosepiece and causes the membrane to oscillate. This oscillation in turn leads to a deformation of the electromechanical transducer. The deformation generates an electric output signal, via which the pressure fluctuation can be detected and evaluated in order to conclude the degree of closure of the velum. As regards the design of such a membrane as a sensor, reference is made to EP 1 304 131 A1, in which the membrane is used as a "respiration sensor". It is, however, alternatively also conceivable to use a separate pressure sensor instead of the membrane of the nebuliser as the first pressure sensor. This is in particular also to be provided in the case of a nozzle nebuliser, which does not comprise such a membrane.

The evaluation means advantageously controls the aerosol therapy device depending on the degree of closure. That is to say, aerosol production and/or the aerosol flow should be triggered/formed or ended depending on the arriving signal strength or the signal displacement due to the degree of closure of the velum. It is thereby ensured that active agent only flows through the nasal cavity when the velum is closed and that deposition of the active agent in the pharyngeal cavity or the lungs is sufficiently minimised or prevented.

It is furthermore advantageous if the evaluation means emits an acoustic and/or optical signal depending on the degree of closure in order to indicate the degree of closure. Coordination when closing the velum is thereby made easier for the user. A type of training mode can also be provided, in which the user can train closure of the velum.

The detected signal of the pressure fluctuation is preferably its frequency and/or pressure. The frequency is in the range of approximately 30 to 50 Hz and is not dependent on the physical conditions of the respective user. A phase shift in the frequency merely occurs depending on the corresponding volumes of the user (nasal cavities). It is, however, alternatively also possible to detect the pressure. In order to accordingly conclude the degree of closure, the frequency or pressure is thereby measured over time and respectively compared with predetermined values.

The use of a sinusoidal pressure fluctuation has proven to be particularly advantageous.

The aerosol therapy device advantageously comprises a second pressure sensor, which detects the signal of the pressure fluctuation that is introduced into the other of the two nostrils of the user via the second nosepiece, whereby the evaluation means compares the signals of the first and second pressure sensors so as to be able to conclude the degree of closure of the velum of the user.

Further advantages and features of the present invention are apparent from the following description of an example embodiment, in which reference is made to the accompanying drawings.

Figure 1:
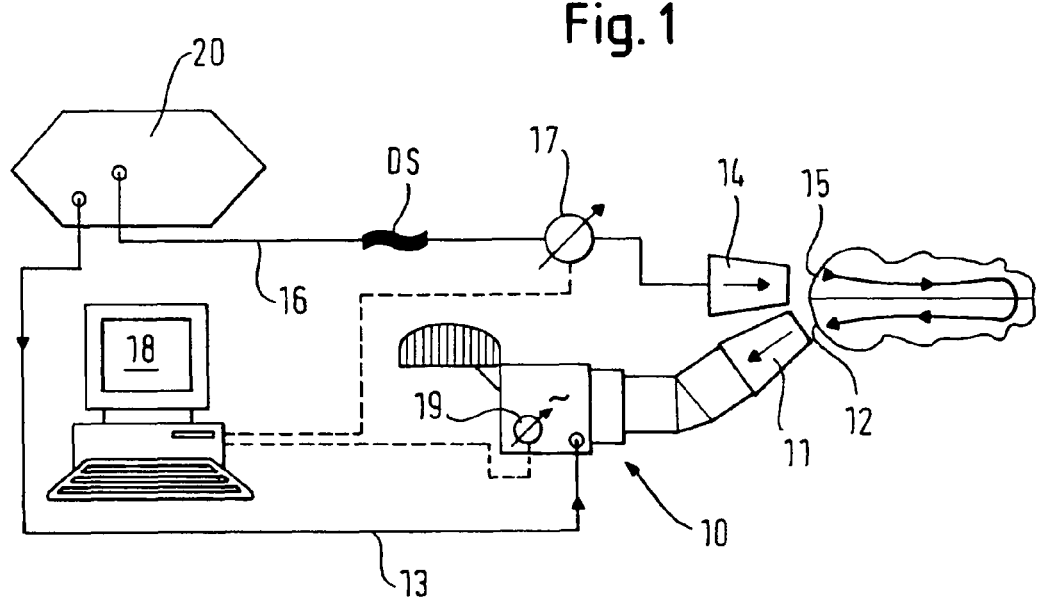
FIG. 1 shows a schematic representation of an aerosol therapy device according to the present invention.

FIG. 1 shows an example of an aerosol therapy device according to an embodiment of the present invention, said device comprising a nebuliser 10. For generating an aerosol, the nebuliser 10 comprises a membrane and an electromechanical transducer—in this case a piezoelectric element—having a functional connection to said membrane. The membrane is caused to oscillate by the electromechanical transducer such that the active agent, which is preferably in liquid form, is nebulised through the membrane into a nebulisation chamber (not shown). This process is also referred to as aerosol production. As regards the design of the membrane that is known per se as well as its later use as a sensor, the person skilled in the art is referred to EP 1 304 131 A1 for further information.

A first nosepiece 11 that is to be tightly fitted to one of the two nostrils 12 of a user is in fluid connection with the nebulisation chamber. In the shown embodiment, the aerosol flow is formed by connecting the nebuliser 10 with a supply unit 20. For this purpose, the supply unit 20 and the nebuliser 10 are connected with one another by means of a compressed air line 13, via which compressed air is introduced into the nebulisation chamber to form the aerosol flow that is introduced into the nostril 12 via the first nosepiece 11.

The aerosol therapy device of the present invention furthermore comprises a second nosepiece 14 that is to be tightly fitted to the other of the two nostrils 15. The second nosepiece 14 is connected with the supply unit 20 via a pressure fluctuation line 16. The supply unit 20 contains a pressure fluctuation source (not shown), via which a sinusoidal pressure fluctuation is generated. The pressure fluctuation is introduced into the nostril 15 via the pressure fluctuation line 16 and the second nosepiece 14.

The aerosol flow and the pressure fluctuation are therefore superimposed in the nasal cavity during operation in order to ensure a preferred deposition of the active agent in the paranasal cavities.

A pressure sensor 17 (second pressure sensor) is furthermore provided in the pressure fluctuation line 16, which detects the pressure fluctuation that is to be introduced—the pressure fluctuation generated by the source. The pressure sensor 17 is connected to an evaluation means 18. The membrane of the nebuliser 10 is also connected to the evaluation means 18. As described in EP 1 304 131 A1, this membrane can be used as a pressure sensor (first pressure sensor). In other words, the pressure fluctuation arriving at the nosepiece 11, which reaches the nebulisation chamber and thus impinges on the membrane, causes the membrane to oscillate, as a result of which the piezoelectric element is deformed and emits an electric signal. This emitted electric signal can be used by the evaluation means 18 to measure the pressure fluctuation. Alternatively, and as is shown in FIG. 1, a separate pressure sensor 19 (first pressure sensor) can also be provided in the nebulisation chamber, the walls thereof or the nosepiece 11 to measure the pressure fluctuation.

As regards the design of the nosepieces and the connection to the nebuliser, reference is made to DE 102 39 321 B3 and the subsequently published DE 10 2006 001 113 B. The same also applies for the means for forming the pressure fluctuation, i.e. the pressure fluctuation source.

The operation of the aerosol therapy device according to the invention as described above will be explained in the following with reference to FIGS. 1 and 2.

During operation, the pressure fluctuation source of the supply means 20 generates a pressure fluctuation which can have a sinusoidal, stepped, pulsed or other form. The pressure fluctuation that is sinusoidal here is introduced into the nostril 15 of the user via the supply line 16 and the second nosepiece 14. The evaluation means 18 measures the introduced pressure fluctuation, labelled in FIG. 2 as A (input amplitude), via the pressure sensor 17. The introduced pressure fluctuation A (input amplitude), labelled in FIG. 1 as DS, propagates from the nostril 15 into the nasal cavity and exits from the nostril 12. From there it flows through the first nosepiece 11 and is detected in the shown example by the pressure sensor 19. The detected signal is emitted to the evaluation unit 18 and can be compared therein with the value of the pressure sensor 17.

Figure 2:
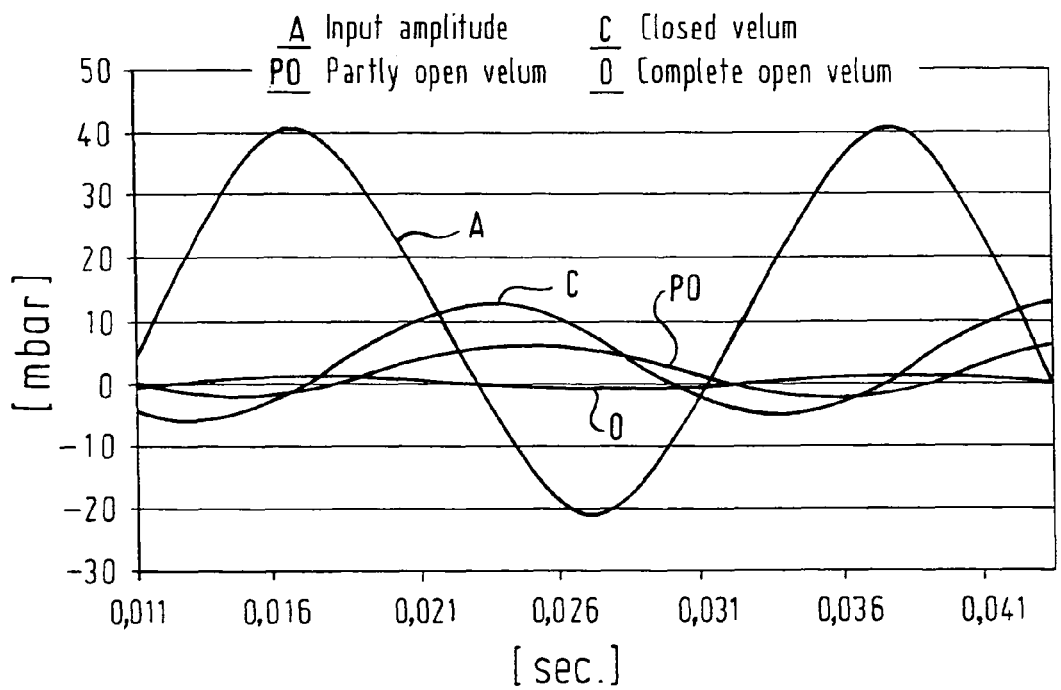
FIG. 2 shows an example representation of the introduced pressure fluctuation as well as of the signal arriving at the first nosepiece when the velum is completely open, partly open and closed, respectively.

If the signal detected by the first pressure sensor 19 corresponds to the pressure fluctuation when the velum is closed, labelled in FIG. 2 as C (closed velum), the aerosol flow will, in the case of continuous aerosol production, be formed and/or triggered by supplying compressed air to the nebulisation chamber via the compressed air line 13. Alternatively, in the case of a continuous supply of compressed air via the compressed air line 13, i.e. a continuous flow, aerosol production can be triggered at this time, i.e. aerosol is generated via the membrane. No such control occurs with pressure fluctuations respectively labelled PO (partly open velum) and O (complete open velum), which correspond to a partly open and a completely open velum. It is furthermore apparent from FIG. 2 that the pressure fluctuation curve becomes flatter over time, i.e. attenuation greatly increases as the degree of opening of the velum increases.

It can furthermore be provided in the device according to the invention that the individual degrees of closure O (complete open velum), PO (partly open velum) and C (closed velum) are indicated by way of different coloured lighting means or on a scale in which, as the degree of closure increases, a lighting means is switched on. The emission of an acoustic signal, possibly a spoken one (closed velum), is also conceivable. The user is thus permitted to train closure of the velum with corresponding feedback from the system.

As is further apparent from FIG. 2, the introduced pressure fluctuation is a sinusoidal pressure fluctuation in the shown embodiment, i.e. the pressure fluctuation has the form of a sinus curve.

As is apparent from the above description, the present invention is based, on the one hand, on introducing the aerosol into one of the two nostrils and the pressure fluctuation into the other of the two nostrils, and measuring the pressure fluctuation accordingly arriving on that side on which the aerosol is introduced, to thereby conclude the degree of closure of the velum. Although the present invention was described above with reference to a particular embodiment, it shall be understood that the invention is defined and restricted exclusively by the following patent claims.

The invention claimed is:

1. Aerosol therapy device comprising:
   a nebuliser for generating an aerosol and forming an aerosol flow,
   a first nosepiece for introducing the aerosol flow into one of the two nostrils of a user,
   a pressure fluctuation source for generating a pressure fluctuation,
   a second nosepiece for introducing the pressure fluctuation into the other of the two nostrils of the user in order to superimpose the pressure fluctuation and the aerosol flow,
   a sensor system comprising a first pressure sensor for detecting a signal of the pressure fluctuation that arrives at the first nosepiece, and
   an evaluation means that concludes the degree of closure of the velum of the user based on said signal.

2. Aerosol therapy device according to claim 1, in which the evaluation means triggers or ends generation of the aerosol and/or formation of the aerosol flow depending on the degree of closure.

3. Aerosol therapy device according to claim 1, in which the evaluation means emits an acoustic and/or optical signal depending on the degree of closure in order to indicate the degree of closure.

4. Aerosol therapy device according to claim 1, in which the detected signal of the pressure fluctuation is its frequency and/or pressure.

5. Aerosol therapy device according to claim 1, in which the sensor system furthermore comprises a second pressure sensor, which detects the signal of the pressure fluctuation that is introduced into the other of the two nostrils of the user via the second nosepiece, the evaluation means comparing the signals of the first and second pressure sensors in order to conclude the degree of closure of the velum of the user.

6. Aerosol therapy device according to claim 1, in which the pressure fluctuation is a sinusoidal pressure fluctuation.

7. Aerosol therapy device comprising:
   a nebuliser for generating an aerosol and forming an aerosol flow,
   a first nosepiece for introducing the aerosol flow into one of the two nostrils of a user,
   a pressure fluctuation source for generating a pressure fluctuation,
   a second nosepiece for introducing the pressure fluctuation into the other of the two nostrils of the user in order to superimpose the pressure fluctuation and the aerosol flow,
   a sensor system comprising a first pressure sensor for detecting a signal of the pressure fluctuation that arrives at the first nosepiece, and
   an evaluation device configured to determine the degree of closure of the velum of the user based on said signal.

* * * * *